United States Patent [19]

Konrad et al.

[11] 4,395,262
[45] Jul. 26, 1983

[54] HAIR DYEING AGENT

[75] Inventors: Eugen Konrad, Darmstadt, Fed. Rep. of Germany; Herbert Mager, Fribourg, Switzerland

[73] Assignee: Wella Aktiengesellschaft, Darmstadt, Fed. Rep. of Germany

[21] Appl. No.: 196,551

[22] PCT Filed: Aug. 2, 1979

[86] PCT No.: PCT/EP79/00060
§ 371 Date: Apr. 16, 1980
§ 102(e) Date: Mar. 6, 1980

[87] PCT Pub. No.: WO80/00417
PCT Pub. Date: Mar. 20, 1980

[30] Foreign Application Priority Data

Feb. 28, 1980 [DE] Fed. Rep. of Germany ....... 2835776

[51] Int. Cl.³ .............................................. A61K 7/13
[52] U.S. Cl. ........................................... 8/410; 8/406; 8/407; 8/408; 8/409; 8/411; 8/412; 8/423
[58] Field of Search ................................ 8/406–412, 8/423

[56] References Cited

U.S. PATENT DOCUMENTS 2,391,137 12/1945 Danuser et al. ................... 260/152

FOREIGN PATENT DOCUMENTS 4366 3/1979 Fed. Rep. of Germany .

*Primary Examiner*—Albert T. Meyers
*Assistant Examiner*—John M. Kilcoyne
*Attorney, Agent, or Firm*—Michael J. Striker

[57] ABSTRACT

Agents for the oxidative dyeing of hair, containing as coupling substance at least one derivative of 1,2-methylene dioxybenzene of the general formula

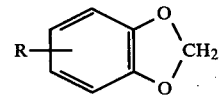

in which R signifies an OH—, NH$_2$—, NHR$^1$— or NR$^1$R$^2$-group, wherein R$^1$ and R$^2$ represent, independently of each other, an alkyl-, hydroalkyl-, or acyl group with 1 to 4 carbon atoms. The coupling substance is contained in these agents in a concentration of about 0.01 to 3.0 percent by weight, i.e. in a mixture with customary developing substances and, in given instances, also customary coupling substances. The particular possibility exists of producing dark natural tints by a mixture of 4-oxy-1,2-methylene dioxybenzene with the developing substance p-aminophenol.

11 Claims, No Drawings

HAIR DYEING AGENT

BACKGROUND OF THE INVENTION

The object of the invention are agents for the oxidative dyeing of hair, characterized by containing as coupling substances derivatives of 1,2 methylenedioxybenzene.

Oxidative colorants have obtained essential importance in the field of hair dyeing. The coloration results herein by a reaction of certain developing substances with certain coupling substances, in the presence of a suitable oxidating agent.

1,4-diaminobenzene, 2,5-diaminotoluene and p-aminophenol are used in particular as developing substances. Mention is to be made of resorcin, 4-chlororesorcin, α-naphthol, m-aminophenol and derivatives of m-phenylenediamine as preferably used coupling substances.

Oxidative colorants used in the dyeing of human hair must satisfy numerous special demands. They must be unobjectionable as to toxicology and dermatology, and allow dyeing to the desired intensity. It is furthermore required that a wide range of different color nuances will be obtained by the combination of suitable developing and coloring components. Furthermore, the resulting coloring should, to a good degree, be fast to light and resistant to permanent wave treatment, acids, and rubbing. Such hair coloring must, at any rate, remain stable against the influence of light, rubbing, and chemical agents for a period of at least 4 to 6 weeks.

The multitude of requirements put forward can, however, not be fully satisfied by oxidative hair dye agents as presently used, and also not by initial coloring stages as recently recommended, such as, for instance, derivatives of pyrimidine.

Endeavoring to obtain an improvement in the toxicological and dermatological aspects relative to agents for the oxidative dyeing of hair based on the developing substances 1,4-diaminobenzene and 2,5-diaminotoluene, attempts are being made at the present time, to increasingly substitute these developing substances by p-aminophenol which is more compatible physiologically. Hair dyeing agents on the basis of p-aminophenol in combination with known couplers can, however, neither produce natural color tints nor can an adequate color intensity be attained. Thus, substitution of, respectively,1,4-diaminobenzene or 2,5-diaminotoluene,by p-aminophenol,has hitherto been possible only in exceptional instances.

The task has therefore been posed to find suitable coupling substances which in combination with the physiologically advantageous developing substance p-aminophenol, will satisfy the requirements regarding naturalness and intensity of the attainable colorations, whilst maintaining the physiological advantages.

SUMMARY OF THE INVENTION

It has now been found that agents for the oxidative coloring of hair, containing at least one derivative of 1,2-methylene dioxybenzene of the general formula:

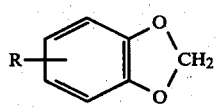

in which R signifies an OH—, $NH_2$—, $NHR^1$— or an $NR^1R^2$— group, wherein $R^1$ and $R^2$ represent, independent of each other, an alkyl-, hydroxyalkyl- or acyl groups with 1 to 4 carbon atoms, will, as coupling substances, satisfy the requirements as set, to a particularly high degree.

Even though use of the aforenamed derivatives of 1,2 methylenedioxybenzene as coupling substances in combination with the developing substance p-aminophenol, is of particular advantage in its physiological aspects, these coupling substances may, conforming to the respective requirements, be contained in the hair dyeing agents as per invention, also in combination with the developing substances 1,4-diaminobenzene, 2,5-diaminotoluene and with further known developing substances or mixtures thereof.

The derivatives of the 1,2 methylenedioxybenzene of the aforenamed formula, contained as coupling substance, are well soluble in water or wateralcohol, and have an excellent shelf life particularly as constituent of the hair dyeing agents as per invention.

The aforenamed coupling substance, of which the 4-oxy-1,2-methylenedioxybenzene (also known under the generic term "Sesamol") is preferred, should be contained in the hair dyeing agents in a concentration of about 0.01 to 3.0 percent by weight, preferably 0.1 to 3.0 percent by weight. The total quantity of the oxidative colorants, consisting of developing substances and coupling substances, should suitably amount to about 0.1 to 5.0 percent by weight, preferably 0.5 to 3.0 percent by weight. All percents given are by weight of total amount of hair dyeing agent.

The coupling components will generally be used in equimolar quantities relative to the developing components. It will, however, be of no disadvantage when the coupling components are present in this relation in a certain excess or deficiency.

Furthermore, the hair dyeing agents of the present application may additionally contain other known coupling substances such as α-naphthol, m-aminophenol, m-phenylenediamine m-toluylenediamine, 2,4-diaminoanisole, 3,4-diaminobenzoic acid and 6-methylene-3-aminophenol and, furthermore, customary direct drawing colorants for instance triphenylmethane colorants such as Diamond Fuchsin (C.I. 42 510) and Leather Ruby HF (C.I. 42 520), aromatic nitro colorants such as 2-nitro-1,4-diaminobenzene, azo dyes such as Acid Brown 4 (C.I. 14 805 and Acid Blue 35 (c.I. 13 385) anthraquinone dyes such as Disperse Violet 4 (C.I. 61 105), Disperse Blue 1 (C.I. 64 500), Disperse Red 15 (C.I. 60 710), Disperse Violet 1 (C.I. 61 100) and also 1,4,5,8-tetra-amino-anthraquinone and 1,4 diamino-anthraquinone.

Apart from the above, the hair dyeing agents may yet also contain further customary cosmetic additives such as, for instance,antioxidants such as ascorbic acid or sodium sulfite, alkaline hydroxides, perfume oils, complex formers, wetting agents, emulgators, thickeners, conserving agents and others. The hair dyeing agent may be prepared as a solution, preferably as a cream, a gel, or an emulsion. The combination will represent a mixture of the coloring components with other constituents customary in such preparation. Customary constituents of creams, emulsions, or gels will, for instance, include wetting agents, or emulgators from the classes of anionic or non-iongenic surfactants such as sulfates of fatty alcohols, alkanolamides of fatty acids, alkyl sulfonates, alkylbenzene sulfonates, ethoxylated fatty alcohols, ethoxylated nonylphenols, and, furthermore thickeners such as higher fatty alcohols, starch, cellulose derivatives, paraffin oil and fatty acids, and still furthermore also conserving agents such as lanolin derivatives, cholesterol and pantothenic acid. The constituents as noted, are used in the amounts customary for such purposes, f.i. the wetting agents and emulgators in concentrations at about 0.5 to 30 percent by weight, whilst the thickeners may be contained in the preparations in quantities of about 0.1 to 25 percent by weight.

Depending upon the composition, the dyeing agents as per invention may react weakly acidic, neutral, or alkaline. They will, in particular, have a pH value in the alkaline range between 8.0 and 11.5, adjustment being preferably made with ammonia. However, certain organic amines, f.i. monoethanolamine or triethanolamine may be used for this purpose.

Their application is made in the manner as known, by mixing the hair dyeing agents with an oxidative agent shortly before use, and applying the mixture onto the hair. It is mainly hydrogen peroxide, for instance as a 6 percent aqueous solution, which is used to develop the hair coloring, or, respectively, its adductive compounds with urea, melamine, or sodium borate. The application temperatures of the hair dyeing agent are in the range of 15° C. to 50° C.

After an application time of about 10 to 45 minutes, preferably about 30 minutes, the hair is rinsed with water and dried. In given instances, washing with a shampoo is made after this rinse and a final rinse made with a weak organic acid such as, f.i., citric acid or tartaric acid.

The dyeing agents as per invention, based upon the initially named derivatives of 1,2-methylenedioxybenzene as coupling substance will lead to hair colorings with excellent fastness properties particularly in respect of fastness to light, washing, and rubbing and they may be withdrawn again with reducing agents.

Regarding the possibilities in respect of coloration, the hair dyeing agents as per invention will, depending upon the type and constitution of the color components, offer a wide range of various color nuances, ranging from blond tones over brown, purple, violet hues and up to blue and black color tints.

The superior coloring properties of the hair dyeing agents as per application will become especially apparent when using 4-oxy-1,2-methylenedioxybenzene as coupling substance. This can be proved particularly when the known coupling substance, resorcin, is replaced by 4-oxy-1,2-methylenedioxybenzene in hair dyeing agents on the basis of p-aminophenol and resorcin. Also, when compared with the use of other known coupling substances, this measure will lead to color tints of essentially more intensive coloring, which are more natural. Thus, use of 4-oxy-1,2-methylenedioxybenzene in the hair dyeing agents as per invention will allow, for the first time, producing of dark natural tints on the basis of p-aminophenol. Beyond this, 4-oxy-1,2-methylenedioxybenzene together with the developing substance 1,4-diaminobenzene and 2,5-diaminotoluene will produce very intensive natural color tints wherein, depending upon the concentration of the two initial dyeing stages, blond to dark brown colorations may be obtained. It is of particular importance herein, that 4-oxy-1,2-methylenedioxybenzene combined with respectively 1,4-diaminobenzene or 2,5diaminotoluene, will be effective as a nuancing agent, already in comparatively low concentrations.

In summing up, it may be stated that use of the hair dyeing agent as per invention, with a content of the aforenoted derivatives of 1,2-methylenedioxybenzene as coupling substance, will considerably increase the present possibilities of producing coloring nuances by oxidating, wherein, particularly by making available more intensive colorations on the basis of the developing substance p-aminophenol, hair dyeing agents have been obtained which are of an improved physiological compatibility.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

Hair dyeing solution

| | |
|---|---|
| 2.0 g | 4-oxy-1,2-methylene dioxybenzene |
| 2.0 g | p-aminophenol |
| 0.8 g | sodium hydroxide, solid |
| 0.4 g | sodium sulfite, anhydrous |
| 10.0 g | diglycolether sulfate of lauryl alcohol, 28% aqueous solution |
| 10.0 g | isopropanol |
| 20.0 g | ammonia, 10% |
| 54.8 g | water |
| 100.0 g | |

50 g of the hair dyeing agent as above are mixed with 50 mL of a 6% solution of hydrogen peroxide shortly before using, and the mixture then applied to blond human hair. After an application period of 30 minutes at 30° C., rinsing is made with water and drying thereafter. The hair has obtained a medium brown color tint with yellowish reflections.

EXAMPLE 2

Hair dyeing agent as a gel

| | |
|---|---|
| 0.6 g | 4-oxy-1,2-methylene dioxybenzene |
| 0.4 g | 1,4-diaminobenzene |
| 0.3 g | sodium hydroxide, solid |
| 0.4 g | sodium sulfite, anhydrous |
| 15.0 g | oleic acid |
| 7.0 g | isopropanol |
| 10.0 g | ammonia, 22% |
| 66.3 g | water, fully desalinated |
| 100.0 g | |

50 g of this hair dyeing agent are mixed with 50 mL hydrogen peroxide solution (6%), shortly before using, and the mixture allowed to act upon blond human hair for 30 minutes at 40° C. Rinsing with water is made thereafter and drying performed. The hair has become dyed in a natural medium brown tint.

EXAMPLE 3

Hair dyeing agent as cream

| | |
|---|---|
| 0.3 g | 4-oxy-1,2-methylene dioxybenzene |
| 0.4 g | p-aminophenol |
| 0.2 g | α-naphthol |

| | |
|---|---|
| 0.2 g | sodium hydroxide, solid |
| 0.3 g | sodium sulfite, anhydrous |
| 3.5 g | diglycolether sulfate of lauryl alcohol 28% aqueous solution |
| 15.0 g | cetyl alcohol |
| 10.0 g | ammonia, 22% |
| 70.1 g | water |
| 100.0 g | |

50 g of the above hair dyeing agent are mixed with 50 mL hydrogen peroxide solution (6%) shortly before use. The mixture is subsequently applied onto blond human hair and allowed to act for 30 minutes at 40° C. Rinsing with water and drying are made thereafter. The hair has obtained a reddish—medium blond coloring.

All percentages quoted in the present application represent percents by weight.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Composition for the oxidative dyeing of hair, comprising a combination of at least one developing substance and at least one coupling substance, comprising as coupling substance at least one derivative of 1,2-methylene dioxybenzene of the general formula

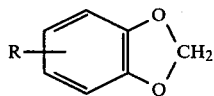

in which R signifies an OH—, $NH_2$—, $NHR^1$—, or $NH^1R^2$— group wherein $R^1$ and $R^2$ represent, independent of each other, an alkyl or hydroxyalkyl group with 1 to 4 carbon atoms.

2. Composition according to claim 1, characterized by containing as coupling substance 4-hydroxy-1,2-methylenedioxybenzene.

3. Composition according to claim 1, characterized by containing the coupling substance in a concentration of about 0.01 to 3.0% by weight of the composition.

4. Composition according to claim 3, characterized by containing the coupling substances in a concentration of about 0.1 to 3.0 percent by weight of the composition.

5. Composition according to claim 1, characterized by containing one of the developing substances selected from the group consisting of 1,4-diaminobenzene, 2,5-diaminotoluene and p-aminophenol.

6. Composition according to claim 1, characterized by also containing a customary coupling substance selected from the group consisting of α-naphthol, m-aminophenol, m-phenylenediamine, m-toluylenediamine, 2,4-diaminoanisole, 3,4-diaminobenzoic acid and 6-methylene-3-aminophenol.

7. Composition according to claim 1, characterized by the total quantity of the combination of developing substance and coupling substance amounting to 0.1 to 5.0% by weight of the composition.

8. Composition according to claim 7, characterized by the total quantity of the combination of developing substance and coupling substance amounting to about 0.5 to 3.0% by weight of the composition.

9. Composition according to claim 1, further comprising a direct drawing colorant selected from the group consisting of Diamond Fuchsin (C.I. 42 510), Leather Ruby HF (C.I. 42 250), 2-nitro-1,4-diaminobenzene, Acid Brown 4 (C.I. 14 805), Acid Blue 35 (C.I. 13 385), Disperse Violet 4 (C.I. 61 105), Disperse Blue 1 (C.I. 64 500), Disperse Red 15 (C.I. 60 710), Disperse Violet 1 (C.I. 61 100), 1,4,5,8-tetra-amino-anthraquinone and 1,4-diamino anthraquinone.

10. Composition according to claim 1, further comprising antioxidants.

11. Composition according to claim 10, wherein said antioxidants are selected from the group consisting of ascorbic acid and sodium sulfite.

* * * * *

UNITED STATES PATENT AND TRADEMARK OFFICE
CERTIFICATE OF CORRECTION

PATENT NO. : 4 395 262
DATED : July 26, 1983
INVENTOR(S) : Eugen Konrad and Herbert Mager It is certified that error appears in the above—identified patent and that said Letters Patent is hereby corrected as shown below:

On the title page:
In the heading [30] the filing date of the German application should read:
        --August 16, 1978--

Signed and Sealed this

First Day of November 1983

[SEAL]

Attest:

GERALD J. MOSSINGHOFF

Attesting Officer     Commissioner of Patents and Trademarks